United States Patent [19]

McCarthy et al.

[11] 4,069,347
[45] Jan. 17, 1978

[54] COMPOSITIONS OF QUATERNARY AMMONIUM DERIVATIVES OF LANOLIN ACIDS

[75] Inventors: Justin P. McCarthy, Carteret; Mitchell L. Schlossman, Rockaway, both of N.J.; Lee R. Mores, Cincinnati, Ohio

[73] Assignee: Emery Industries, Inc., Cincinnati, Ohio

[21] Appl. No.: 711,088

[22] Filed: Aug. 2, 1976

[51] Int. Cl.$^2$ .............................................. A61K 7/08
[52] U.S. Cl. ...................................... 424/358; 424/70
[58] Field of Search ......................... 424/70, 358, 320; 260/404.5 Q

[56] References Cited

U.S. PATENT DOCUMENTS

| 2,583,772 | 1/1952 | Grunderson | 260/404.5 Q |
|---|---|---|---|
| 2,668,165 | 2/1954 | Carpenter | 260/404.5 Q |
| 2,935,474 | 5/1960 | Kirkpatrick et al. | 260/404.5 Q |
| 3,001,996 | 9/1961 | Mannheimer | 260/404.5 Q |
| 3,970,759 | 7/1956 | Frankenfeld et al. | 424/70 |

FOREIGN PATENT DOCUMENTS

| 3,572 | 5/1971 | Japan | 424/358 |
|---|---|---|---|
| 915,816 | 1/1963 | United Kingdom | 424/358 |

*Primary Examiner*—Dale R. Ore
*Attorney, Agent, or Firm*—Gerald A. Baracka; John D. Rice

[57] ABSTRACT

Improved quaternary ammonium compositions are provided wherein quaternized ammonium derivatives of lanolin acids are combined with specific branched-chain diols. These compositions exhibit improved water solubility and have excellent compatibility with anionic emulsifiers and surfactants which make them extremely useful for the preparation of clear cosmetic formulations.

13 Claims, No Drawings

COMPOSITIONS OF QUATERNARY AMMONIUM DERIVATIVES OF LANOLIN ACIDS

BACKGROUND OF THE INVENTION

Quaternary ammonium derivatives of acylated alkylenediamines are known (see for example, U.S. Pat. Nos. 1,737,458; 2,303,191; 2,589,674; 2,958,213 and 3,766,267) and exhibit varying degrees of water solubility and compatibility with other ingredients depending on the particular acylating agent, diamine and quaternizing agent used. Insolubility and incompatibility are a particular problem when the acyl moiety is derived from mixed higher fatty acids, such as acids derived from animal and vegetable sources. Quaternary ammonium derivatives of lanolin amides, for example, have heretofore typically exhibited poor compatibility with other ingredients commonly used in cosmetic formulations such as anionic emulsifiers and surfactants. Also, aqueous solutions of these lanolin "quats" have become cloudy or formed a precipitate after very short periods of time. It would be highly advantageous and desirable if the compatibility and water solubility of quaternary ammonium derivatives of lanolin amides could be improved.

SUMMARY OF THE INVENTION

We have now quite unexpectedly discovered that if quaternized ammonium derivatives of lanolin amides (referred to herein as lanolin "quats") are combined with specific branched-chain diols that improved compatibility with water and other compounds typically used in cosmetic formulations is obtained. This discovery now makes it possible to obtain unlimited water solubility of lanolin quats. As a result, the cosmetic formulator is now able to use relatively high concentrations of the quaternary compound in clear formulations whereas before only very low levels of the quat could be tolerated due to the insolubility of the quat in water. When used in conjunction with the branched-chain diols the lanolin quats also exhibit good compatibility with anionic surfactants, a feature which is necessary for the preparation of acceptable clear formulations. As a result of this invention it is now possible to obtain highly clear shampoo and clear hair rinse formulations having high concentrations of the quaternary ammonium compound.

The lanolin quats used for this invention are derived from lanolin acids, preferably, refined lanolin acids, which are reacted with a diamine having one tertiary amine group with the remaining amine function being either a primary or secondary amine. Dimethylaminopropylamine, diethylaminopropylamine, dimethylaminoethylamine and diethylaminoethylamine are especially useful for this purpose. The resulting lanolin amide is treated with a suitable quaternizing agent such as an aliphatic halide, aralkyl halide, ethylene chlorohydrin or alkyl sulfate. The branched-chain diols employed in combination with the lanolin quat are aliphatic, saturated diols containing from 5 to 20 carbon atoms with at least 3 carbon atoms separating the hydroxyl groups. These diols contain at least two alkyl branches totaling at least 3 carbon atoms with at least one of the alkyl groups attached to the carbon atom immediately adjacent to one of the hydroxyl groups. The amount of diol employed will range between about 35 and 75 wt. %, and more preferably from 40 to 65 wt. %, based on the weight of the blend. Especially useful compositions are obtained by blending 2-methyl-2,4-pentanediol or 2-ethyl-1,3-hexanediol with lanolin quats of the formula

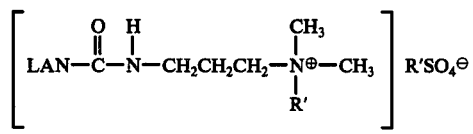

wherein LAN represents the radicals derived from lanolin fatty acids and R' is a methyl or ethyl radical. Aqueous solutions of these blends containing between about 25 and 75% by weight of the quat/diol blend are particularly useful for the preparation of clear cosmetic formulations.

DETAILED DESCRIPTION

This invention relates to improved compositions comprising a quaternary ammonium compound of an acylated alkylenediamine derived from lanolin acids and a branched-chain diol. The branched-chain diol serves as a solubilizing and compatibilizing agent for the lanolin quat. This invention has as it principal object to provide improved aqueous compositions of lanolin quats which do not become cloudy or form a precipitate upon standing and which can be utilized for the preparation of clear cosmetic formulations. Still another object of this invention is to provide stable aqueous solutions having a high concentration of lanolin quats.

This invention deals with quaternary ammonium derivatives of acylated alkylenediamines which correspond to the general formula (I)

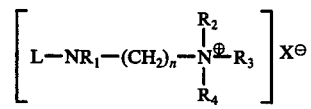

wherein L represents the acyl radicals derived from lanolin fatty acids, $R_1$ is hydrogen or a $C_{1-4}$ alkyl group, $R_2$ and $R_3$ are $C_{1-4}$ alkyl groups, $R_4$ is a radical selected from the group consisting of alkyl, aralkyl, hydroxyalkyl and unsaturated aliphatic hydrocarbon radicals, X is an anion such as halide, nitrate, sulfate, alkylsulfate, alkylphosphate and the like, and $n$ is an integer from 2 to 5. The quaternary ammonium compounds are obtained by reacting the acid chloride of the lanolin acid with a suitable diamine to obtain the lanolin amide and then combining the lanolin amide with the quaternizing agent. It is also possible to directly react the lanolin fatty acid with a suitable diamine and then the quaternizing agent. In a preferred embodiment of this invention $R_1 = H$, $n = 3$, $R_2$, $R_3$ and $R_4$ are methyl or ethyl groups and X is a $CH_3SO_4^-$ or $C_2H_5SO_4^-$ radical.

Lanolin acids used for the preparation of the quats are obtained by conventional procedures typically by saponifying lanolin (wool fat) and separating the soaps from the unsaps. The soaps are then acidulated to recover the lanolin acids which consist primarily of n-alkanoic acids, iso-alkanoic acids and hydroxy-alkanoic acids. Refined lanolin acids obtained by distillation of the technical lanolin acids obtained by the above-described saponification procedure are particularly useful for this invention. The refined lanolin acids may also be bleached or decolorized to further improve the quality of the resulting acid mix. Conventional refining (distillation) procedures can be employed for the preparation of the refined acids, however, distillation using a wiped-film evaporator such as described in U.S. Pat. No. 3,270,850 is particularly useful for this purpose. Particularly useful refined lanolin acids melt in the range 40°–50° C and have acid and hydroxyl values of 140–150 and 30–45, respectively.

Diamines reacted with the lanolin acid or lanolin acid halide to obtain the lanolin amide have one tertiary amine group. The remaining amine function can be either a primary or secondary amine. Useful diamines of this type correspond to the general formula (II)

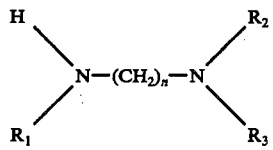

wherein $R_1$ is hydrogen or a $C_{1-4}$ alkyl group, $R_2$ and $R_3$ are $C_{1-4}$ alkyl groups and $n$ is an integer from 2 to 5, preferably, 2 or 3. Especially useful diamines for the preparation of the lanolin quats are dimethylaminopropylamine, diethylaminopropylamine, dimethylaminoethylamine and diethylaminoethylamine.

Suitable quaternizing agents include aliphatic halides such as methyl chloride, methyl bromide, methyl iodide, ethyl chloride, ethyl bromide, iso-propyl bromide and butyl bromide, aralkyl halides such as benzyl chloride or benzyl bromide, ethylene chlorohydrin and alkyl sulfates such as diethyl or dimethyl sulfate.

Especially useful for this invention are quats corresponding to the structural formula (III)

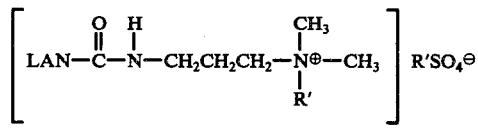

where LAN represents the radicals derived from refined lanolin fatty acids and R' is a methyl or ethyl group. These quats form highly useful aqueous solutions when employed in conjunction with a branched-chain diol in accordance with the teachings of this invention which are particularly effective for the preparation of clear shampoo and clear hair rinse formulations.

The branched-chain diols used in conjunction with the lanolin acid quats are aliphatic, saturated diols having at least 5 and up to about 20 carbon atoms but preferably 6 to 12 carbon atoms with at least 3 carbon atoms separating the hydroxyl groups and at least two alkyl groups totaling at least three carbon atoms and one of which is attached to the carbon atom immediately adjacent to one of the hydroxyl groups. The $C_{5-20}$ diols correspond to the structural formula (IV)

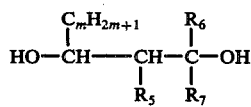

where $m$ is an integer from 1 to 5 and at least one of the groups $R_5$, $R_6$ or $R_7$ is a $C_{1-4}$ alkyl group with the remainder of the R groups being hydrogen or an alkyl group having 1 to 4 carbon atoms. The diols are typically liquids at room temperature or below. Especially useful aliphatic branched-chain diols for this invention are 2-methyl-2,4-pentanediol and 2-ethyl-1,3-hexanediol. The lanolin quat and the diol are easily blended using conventional mixing procedures. While they can be combined in any proportion for the purpose of this invention the amount of the diol will usually range between about 35 and 75 wt. %, based on the weight of the total blend. Best results are obtained, however, using 40–65 wt. % of the branched-chain diol. The diol may also be present during the formation of the quat.

Using the above-defined lanolin quat/branched-chain diol compositions it is possible to obtain highly useful, clear, stable aqueous solutions. These compositions can be mixed with water in all proportions and the resulting aqueous solutions, particularly those containing between about 25 and 75% by weight of the quat-diol blend, are capable of standing for prolonged periods without settling or becoming cloudy. These aqueous solutions are readily compatible with other cosmetic ingredients including conventional anionic emulsifiers and surfactants and are advantageously employed in the preparation of clear formulations, especially clear shampoo and clear hair rinse formulations.

The following examples illustrate the invention more fully. In these examples all parts and percentages are on a weight basis unless otherwise indicated.

EXAMPLE I 333 grams (1 mole) refined lanolin fatty acids were charged to a glass reaction vessel equipped with a stirrer, thermometer, dropping funnel and condenser/trap arrangement. The mixture was heated with stirring to 105°–115° C under a nitrogen atmosphere while adding 110 grams (1.08 mole) dimethylaminopropylamine over a period of about 15 minutes during which time the temperature increased to about 135° C. The temperature of the reaction mixture was then increased to 150° C and maintained for about 3 hours after which time the acid value of the mixture was 27.6 and the amine value (total) was 140.8. An additional 20 grams dimethylaminopropylamine was then added and the reaction continued for 6½ hours at 150° C. A vacuum was pulled on the system during the final 4 hours of the reaction and for the last hour of reaction the temperature was increased to 160° C and the pressure reduced to about 1 mm Hg. The final product had an acid value of 10, total amine value of 137.8 and tertiary amine value of 137.3.

A portion of the resulting lanolin amide (146.2 grams) was charged with 49 grams isopropanol to a resin kettle equipped with a condenser, stirrer, thermometer and dropping funnel. The reaction mixture was heated with stirring to about 70° C under a nitrogen atmosphere and 46.7 grams benzyl chloride added over a period of about 10 minutes. The reaction temperature was then maintained at 95°–105° C for 2½ hours after which time the amine value was reduced to 0.7. An additional 0.3 grams benzyl chloride was added and the heating continued at 100° C for 2 more hours to reduce the amine value to 0.25. Isopropanol was then removed from the reaction mixture by heating at 100°–110° C for 1 hour under reduced pressure (0.1 mm Hg). Analysis indicated 80% quaternization.

EXAMPLE II

Refined lanolin acids (400 grams) 1.4 moles were charged to a reactor and heated to 135°–140° C under a nitrogen atmosphere while adding 177 grams (1.4 moles) dimethylaminopropylamine over a 10-15 minute period. The reaction mixture was then heated to 155°-160° C for about 3 hours and the pressure reduced to 90-100 mm Hg. for about 45 minutes and then finally to about 1 mm Hg. for 1 hour. The reaction mixture was cooled to 120° C, sparged with water vapor for about 90 minutes and then dried to recover the light tan, semi-solid lanolin amide.

EXAMPLE III

A lanolin amide (444 grams) prepared as described in Example II was charged to a reactor and heated at 60°-70° C. 138 Grams benzyl chloride was added over a period of 1 hour and the reaction mixture maintained at 110° C for about 3 hours. For about the last 45 minutes of reaction the pressure was reduced to 1-2 mm Hg. The reaction mixture was then combined with approximately an equal amount of chloroform and about 10% of a acidic diatomaceous earth, refluxed for about 1 hour, filtered and the solvent evaporated. The final product (79.3% quat) had an amine value of 6.9 and acid value of 9.2

EXAMPLE IV

Lanolin amide prepared in accordance with Example II was heated to 80° C and essentially an equimolar amount of diethylsulfate slowly added over a period of about 1 hour. The temperature was maintained at 110° C for 3-4 hours and the pressure reduced to 1-2 mm Hg during the final stages of heating. The final product contained 77.2% quat.

A 25% active aqueous solution of the quat was prepared by warming a pre-weighed amount of distilled water on a steam bath and adding thereto a small amount of the quat with vigorous stirring. Further additions of the quat were made only after the previously added amount was totally dissolved. The resulting clear, dark amber solution had a pH of 1.95. Upon standing overnight a heavy precipitate formed in solution. Attempts to remove the precipitate by filtration were only partially successful and some cloudiness remained in the filtrate.

To 50 grams of a freshly prepared 25% active aqueous solution of the above quat was added 10 grams hexylene glycol (2-methyl-2,4-pentanediol). The mixture was heated until clear and then allowed to stand for 1 week at room temperature. The solution remained clear and no precipitate was formed. In a similar manner, 50 gram portions of freshly prepared 25% active quat solutions were combined with 10 grams of the following hydroxylic compounds: methanol, isopropanol, propanol, propylene glycol, 1,3-butylene glycol, glycerine and polyoxyethylene glycol-400. Each solution was heated until clear and then allowed to stand at room temperature for 1 week. Varying degrees of precipitate formation was observed in each of these seven solutions before completion of the 7 day test period.

EXAMPLE V

148 Grams dimethylaminopropyl lanolin acid amide was combined with 164 grams hexylene glycol and heated to about 60° C. Diethylsulfate (57.3 grams) was then added dropwise over a 40 minute period. With continued heating (110° C) and after the addition of 2.0 gram diethylsulfate the amine value was reduced to zero. Analysis of the resulting solution indicated 42.86% quat. The resulting clear amber solution was readily miscible with water at room temperature and was diluted to obtain a 25% active (quat) aqueous solution which retained its clarity for more than 3 weeks at room temperature.

EXAMPLE VI

In a manner similar to that described in Example V, 76.5 grams dimethylaminopropyl lanolin acid amide (amine value 135) and 89.6 grams 2-ethyl 1,3-hexanediol was heated and 28.4 grams diethyl sulfate slowly added. The reaction mixture was heated at 100° C until the final amine value was less than 0.1. The resulting clear, amber viscous solution contained 39.3% quat by analysis. This solution was readily miscible with room temperature water in all proportions and a 25% active aqueous solution was extremely stable and showed no signs of cloudiness or precipitate formation even after a prolonged period of storage at room temperature.

EXAMPLE VII

A composition of lanolinamidopropyldimethylethylammonium ethosulfate and hexylene glycol obtained in accordance with the procedure of Example V was diluted with water to prepare a clear aqueous solution containing 25% of the quat. The pH of the 25% active aqueous quat solution was about 4.5 and the solution had a specific gravity of 0.997. To demonstrate the utility of the aqueous solution for the preparation of the clear cosmetic formulations a low pH clear shampoo was prepared by blending 30 parts of an amphoteric imidazoline (Miranol $H_2M$), 8 parts triethylamine salt of lauryl sulfate, 5 parts lauric diethanolamide and 12 parts of the aqueous quat solution. These ingredients were mixed at 70° C until homogeneous, cooled to 40° C and 6.5 parts propylene glycol and a small amount of perfume added with mixing until the mixture was clear. 38.5 Parts deionized water was then added and the pH adjusted to 5 by the addition of lactic acid. The resulting shampoo formulation remained clear even after prolonged storage at room temperature and exhibited excellent stability at elevated temperatures. No phase separation was observed at temperatures up to 120° F even after 4 weeks aging. The shampoo also exhibited good foaming characteristics and imparted substantivity to the hair.

EXAMPLE VIII

A clear hair rinse formulation was prepared as follows: 3.5 parts of the lanolin quat solution of Example VII was stirred with 86.25 parts demineralized water and a 2% solution of hydroxypropyl methylcellulose. An amount of perfume and color additive sufficient to impart the desired properties were then blended into the mixture. The resulting clear and uniform hair rinse formulation imparted excellent properties to hair swatches treated therewith. For example, hair swatches bleached for 20 minutes with Clairol "Summer Blond" and then treated with the hair rinse formulation exhibited much less drag upon wet combing and much improved body, feel and softness than identically bleached swatches not treated with the hair rinse.

EXAMPLE IX

A clear conditioning hair rinse was also prepared using the 25% active quat solution of Example VII. The ingredients used were as follows:

| | |
|---|---|
| Lanolin quat | 2.0 parts |

| -continued | | |
|---|---|---|
| Ethoxylated (16 E.O.) ether | | |
| lanolin alcohols | 6.0 | parts |
| Demineralized water | 91.9 | parts |
| Methyl paraben | 0.1 | part |

All of the above ingredients were heated to approximately 60° C and mixed until clear. The mixture was then allowed to cool to about 20° C and a small amount of perfume added.

EXAMPLE X

To demonstrate the versatility of the present compositions an after shave lotion was prepared by blending 64.4 parts deionized water, 0.4 part of the 25% active quat solution of Example VII and 35.2 parts anhydrous denatured ethyl alcohol (SDA-40) containing a small amount of perfume.

EXAMPLE XI

A cream rinse was prepared in accordance with the following recipe:

| | | |
|---|---|---|
| Quat solution of Example VII | 12.0 parts | |
| Glyceryl stearate (self-emulsifiable) | 12.5 parts | |
| Hydroxypropyl methylcellulose (1% aq. soln.) | 40.0 parts | |
| Deionized water | 46.5 parts | |

The glyceryl stearate and water were combined and heated with stirring to 75° C. This mixture was cooled to 30° C with slow continued stirring and the hydroxypropyl methylcellulose and quat solution then blended in with a small amount of perfume. The pH of the formulation was then adjusted to 5.5 by the addition of lactic acid. The cream rinse formulation improved hair manageability and significantly reduced static charge left on the hair by shampooing, drying and combing. To demonstrate the improvement obtained with this cream rinse formulation, a salon half-head study was conducted on six girls having shoulder length virgin hair. After shampooing, half the hair was rinsed with the above-prepared cream rinse formula and the other half rinsed with a similar cream rinse formula prepared using stearyl dimethyl benzyl ammonium chloride, a quaternary compound commonly used throughout the industry in hair rinse formulations. Five of the six girls preferred the side with the cream rinse prepared using the quat solution of Example VII.

We claim:

1. An improved quaternary ammonium composition comprising (a) 35–75 weight percent of an aliphatic, saturated, branched-chain diol having from 5 to 20 carbon atoms with at least three carbon atoms separating the hydroxyl groups and at least two alkyl groups having a total of at least three carbon atoms, one of the alkyl groups being attached to the carbon atom immediately adjacent to one of the hydroxyl groups, and (b) 25–65 weight percent of a quaternary ammonium compound of the formula

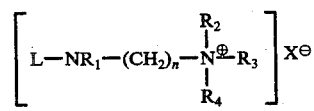

where L represents the acyl radicals derived from lanolin fatty acids, $R_1$ is hydrogen or an alkyl group containing one to four carbon atoms, $R_2$ and $R_3$ are $C_{1-4}$ alkyl groups, $R_4$ is a group selected from the group consisting of alkyl, aralkyl, hydroxyalkyl and unsaturated aliphatic hydrocarbon radicals, X is an anion selected from the group consisting of halide, nitrate, sulfate, alkylsulfate and alkylphosphate and $n$ is an integer from 2 to 5.

2. The composition of claim 1 wherein the quaternary ammonium compound is derived from refined lanolin acids.

3. The composition of claim 1 wherein the branched-chain diol has the formula

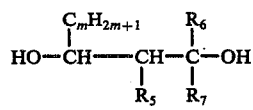

wherein $m$ is an integer from 1 to 5 and at least one of the groups $R_5$, $R_6$ or $R_7$ is an alkyl group containing one to four carbon atoms with the remaining R groups being hydrogen or an alkyl group containing one to four carbon atoms.

4. The composition of claim 3 containing 40–65 weight percent of the branched-chain diol and 35–60% by weight of a quaternary ammonium compound from refined lanolin acids.

5. The composition of claim 4 wherein the quaternary ammonium compound has the formula

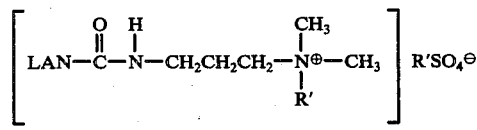

where LAN represents the radicals derived from refined lanolin fatty acids and R' is a methyl or ethyl radical.

6. The composition of claim 5 wherein the refined lanolin fatty acids have an acid value of 140–150, hydroxyl value of 30–45 and melt in the range 40°–50° C.

7. The composition of claim 6 wherein the branched-chain diol is 2-methyl-2,4- pentanediol.

8. The composition of claim 6 wherein the branched-chain diol is 2-ethyl-1,3-hexanediol.

9. A clear aqueous solution containing 25–75 weight percent of a water soluble composition comprising (a) 35–75 weight percent of an aliphatic, saturated branched-chain diol having from 6 to 12 carbon atoms and having the formula

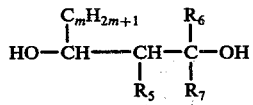

wherein $m$ is an integer from 1 to 5 and at least one of the groups $R_5$, $R_6$ or $R_7$ is an alkyl group containing one to four carbon atoms with the remainining R groups being hydrogen or an alkyl radical containing from one to four carbon atoms and (b) 25–65 weight percent of a quaternary ammonium compound derived from refined lanolin acids and having the formula

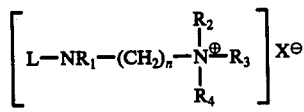

wherein L represents the acyl radicals derived from the refined lanolin acids, $R_1$ is hydrogen or an alkyl group containing one to four carbon atoms, $R_2$ and $R_3$ are alkyl groups containing one to four carbon atoms, $R_4$ is a radical selected from the group consisting of alkyl, aralkyl, hydroxyalkyl and unsaturated aliphatic hydrocarbon radicals, X is an anion selected from the group consisting of halide, nitrate, sulfate, alkyl sulfate and alkylphosphate and $n$ is an integer from 2 to 5.

10. The aqueous solution of claim 9 wherein the water soluble composition contains 40–65 weight percent of the branched-chain diol and 35–60 weight percent of the quaternary ammonium compound.

11. The aqueous solution of claim 10 wherein the quaternary ammoniun compound has the formula

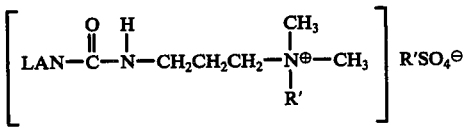

where LAN represents the radicals derived from refined lanolin fatty acids having an acid value of 140–150, hydroxyl value 30–45 and melting in the range 40°–50° C and R' is a methyl or ethyl radical.

12. The aqueous solution of claim 11 wherein the branched-chain diol is 2-methyl-2,4-pentanediol.

13. The aqueous solution of claim 11 wherein the branched-chain diol is 2-ethyl-1,3 hexanediol.

* * * * *